United States Patent [19]
Kawai et al.

[11] Patent Number: 5,802,133
[45] Date of Patent: Sep. 1, 1998

[54] METHOD AND APPARATUS OF X-RAY COMPUTERIZED TOMOGRAPHY

[75] Inventors: Hiroyuki Kawai, Tokyo; Kensuke Sekihara, Musashimurayama, both of Japan

[73] Assignee: Hitachi Medical Corporation, Tokyo, Japan

[21] Appl. No.: 757,996

[22] Filed: Nov. 27, 1996

[30] Foreign Application Priority Data

Dec. 1, 1995 [JP] Japan ................... 7-314196

[51] Int. Cl.$^6$ .................................. A61B 6/03
[52] U.S. Cl. ............................ 378/4; 378/901
[58] Field of Search ........................ 378/4, 901

[56] References Cited

U.S. PATENT DOCUMENTS

| | | | |
|---|---|---|---|
| 4,672,651 | 6/1987 | Horiba et al. | 378/62 |
| 5,383,231 | 1/1995 | Yamagishi | 387/15 |

FOREIGN PATENT DOCUMENTS 8-168487  7/1996  Japan .

OTHER PUBLICATIONS

"Practical cone-beam algorithm", L.A., Feldkamp et al, Optical Society of America, vol. 1, No. 6, 1984, pp.612–619.
"Effects of scattered x-rays on cone–beam 3–D CT images", Magazine of The Institute of Medical Image Information, vol. 12, No. 12, 1995.
"Effects of Scattered X-rays on cone–beam 3–D CT images", SPIC vol. 2163, Phys. of Med. Image, 1994, p. 184.
"Three–Dimensional Imaging–Cone–Beam 3D CT", T. Saito, Med. Imag. Tech. vol. 13, No. 3, May 1995, p. 183.

*Primary Examiner*—David P. Porta
*Assistant Examiner*—David Vernen Bruce
*Attorney, Agent, or Firm*—Fay, Sharpe, Beall, Fagan, Minnich & McKee

[57] ABSTRACT

A method of X-ray computerized tomography whereby a scanner in which an X-ray source for irradiating an X-ray in a cone-beam shape to an object and a two-dimensional detector for detecting the X-ray transmitted through the object are installed is rotated around the object and a projection angle is changed and a distribution of X-ray attenuation coefficients of the object is reconstructed from the transmitted X-ray images obtained at a plurality of projection angles. This method has the steps of: (1) measuring a first transmitted X-ray image measured in a state in which a contrast medium is injected into the object, a second transmitted X-ray image measured in a state in which no contrast medium is injected into the object, and a third transmitted X-ray image measured in a state in which no object is positioned in the apparatus; (2) calculating a first projection image from a difference between logarithms of the first and second transmitted X-ray images obtained at the same projection angle, calculating a second projection image from a difference between logarithms of the second and third transmitted X-ray images obtained at the same projection angle, and simultaneously reconstructing a first reconstructed image from the first projection image and a second reconstructed image from the second projection image in parallel; and (3) composing the first and second reconstructed images, thereby forming a composed image.

17 Claims, 5 Drawing Sheets

METHOD AND APPARATUS OF X-RAY COMPUTERIZED TOMOGRAPHY

BACKGROUND OF THE INVENTION

The invention relates to method and apparatus of X-ray computerized tomography and, more particularly, to method and apparatus of X-ray computerized tomography in which an X-ray source for irradiating an X-ray in a cone-beam shape and a scanner in which a two-dimensional detector for detecting the X-ray is installed are used, the scanner is rotated around an object, a projection angle is changed, projection images from multi-directions around the object are measured, and a distribution of X-ray attenuation coefficients of the object is reconstructed by using the results of the measurement.

FIG. 2 shows a general construction of a conventional cone-beam X-ray computerized tomography apparatus. The cone-beam X-ray computerized tomography apparatus is constructed by a measurement part 1 for measuring and a data processing part 2 for processing the measured data. An X-ray source 4 and a two-dimensional detector 5 are arranged on a scanner 3 of the measurement part 1 at positions which face each other so as to sandwich an object 6.

An X-ray 8 is irradiated in a cone-beam shape from an X-ray focal spot 7 on the X-ray source 4. An intensity of the X-ray transmitted through the object 6 is measured by the two-dimensional detector 5. The scanner 3 is rotated around the object 6 while setting an axis of rotation 9 to the center of rotation. Each time the scanner 3 rotates by a micro angle, a projection of the X-ray and a measurement of the intensity of the transmitted X-ray are performed. The rotation of a micro-angle is repeated the number of times corresponding to the whole circumference, thereby collecting hundred to hundreds of sets of intensity data of the transmitted X-ray. In the following description, an angle of rotation at which the scanner 3 is located in a certain projection is called a "projection angle".

The intensity data of the transmitted X-ray measured by the scanner 3 is converted into digital data and is sent to the data processing part 2. The digital intensity data of the transmitted X-ray is held in memory unit 10. In the data processing part 2, a gamma correction and a geometric distortion correction of the measurement data are first executed in a preprocessing part 11. The corrected data is called a "transmitted X-ray image" hereinafter. In logarithm transform unit 12, a logarithm transform and a correction of the density distortion are executed to the transmitted X-ray image, thereby converting into a "projection image".

On the basis of all of the projection images obtained by performing the foregoing pre-processing, a three-dimensional distribution of X-ray attenuation coefficients in a field of view of the object 6 is reconstructed in a reconstruction part 13. In imaging processing unit 14, the three-dimensional reconstructed image is subjected to visualizing processes such as volume rendering process, maximum intensity projection process, and the like and the processed image is displayed to the operator. As a reconstruction algorithm, L. A. Feldkamp et al., "Practical cone-beam algorithm", J. Opt. Soc. Am. A, Vol. 1, No. 6, pp. 612–619, 1984, or the like is known.

To further explain the above data processing procedure in more detail, FIG. 3 shows a geometrical construction in the cone-beam X-ray computerized tomography apparatus. In FIG. 3, in place of the two-dimensional detector 5, a virtual two-dimensional plane is set at the position corresponding to the detector 5 and is called a "projection plane" 15. The X-ray transmitted through the object 6 forms an image onto the projection plane 15. Although the X-ray focal spot 7 and projection plane 15 rotate around the axis of rotation 9 as a center, a rotation orbital plane of the X-ray focal spot 7 in this instance is called a "midplane" 16.

As shown in FIG. 3, a coordinate system xyz fixed to the object 6 and a coordinate system uv fixed on the projection plane 15 are defined. In case of a projection angle (a), an intensity distribution on the projection plane 15 of the X-ray which was irradiated from the X-ray source 4 and transmitted through the object 6 is measured. As mentioned above, the data that is obtained by performing the gamma calibration and geometric distortion correction to the measurement data is called a "transmitted X-ray image" and is shown by Io(a,u,v). The X-ray irradiated from the X-ray source 4 without positioning any object 6 is directly measured on the projection plane 15 and the measurement data is called an "air scan image" and is shown by Ii(a,u,v). The transmitted X-ray image obtained by injecting a contrast medium into the body of the object 6 by using a catheter 17 and a contrast injector 18 or by a drip at the time of measurement in order to enhance the contrast a blood vessel of interest is, particularly, called a "live image".

In the logarithm transform means 12, a difference between the logarithm of the transmitted X-ray image and the logarithm of the air scan image is calculated, thereby obtaining the projection image. The projection image is shown by P(a,u,v). The logarithm transformation assumes $$P(a,u,v)=\log\{Ii(a,u,v)\}-\log\{Io(a,u,v)\}$$

where, log(x) indicates a natural logarithm of x.

Subsequently, in the reconstruction part 13, an X-ray attenuation coefficient distribution f(x,y,z) of the object is calculated from the whole projection images by the cone-beam reconstruction algorithm of Feldkamp mentioned above. The cone-beam reconstruction calculation can be divided into two stages of 1) a filtering process and 2) a backprojection calculation.

First, in the filtering process, the projection image P(a,u,v) is corrected by a filtering function h(u) of a Shepp-Logan Filter or the like and a filtered projection image Q(a,u,v) is obtained by the following equation (1). FFT{ } and iFFT{ } in the equation (1) denote a Fourier transform and an inverse Fourier transform regarding (u). Since a transformation of discrete data is executed, a Fast Fourier Transform algorithm is used. As shown in FIG. 3, SID indicates a distance between the X-ray source and the detector and SOD denotes a distance between the X-ray source and the rotation center.

$$Q(a, u, v) = iFFT\left\{ FFT\left\{ \frac{SOD}{\sqrt{SOD^2 + u^2 + v^2}} P(a, u, v) \right\} \cdot FFT\{h(u)\} \right\} \quad (1)$$

In the backprojection calculation, the X-ray attenuation coefficient distribution f(x,y,z) of the object is obtained from the filtered projection image Q(a,u,v) by the following equation (2). At this time, in the projection angle (a), a point (u',v') to be backprojected for a point (x,y,z) is called "backprojection coordinates" of the point (x,y,z).

$$f(x, y, z) = \int_0^{2\pi} \frac{SOD^2}{(SOD + x\cos(a) + y\sin(a))^2} Q(a, u', v') da \qquad (2)$$

where, $$u' = \frac{SID}{SOD + x\cos(a) + y\sin(a)} \cdot (-x\sin(a) + y\cos(a))$$

$$v' = \frac{SID}{SOD + x\cos(a) + y\sin(a)} \cdot z$$

SUMMARY OF THE INVENTION

The reconstructed image obtained with the conventional cone-beam computerized tomography apparatus and method is inferior to the reconstructed image derived by a conventional fan-beam X-ray computerized tomography apparatus and method with respect to a density resolution. This is because the following reasons can be mentioned. Namely, the two-dimensional detector 5 of a good performance cannot be obtained, it is difficult to strictly perform a correction of the density distortion of the two-dimensional detector 5, a field of view of the two-dimensional detector 5 is narrow, an influence by scattered X-rays is large (with respect to the influence by the scattered X-rays, refer to Nobuyuki Nakamori et al., "Effects of scattered x-rays on cone-beam 3-D CT images", Magazine of The Institute of Medical Image Information, Vol. 12, No. 12, 1995, and K. Inoue et al., "Effects of Scattered X-rays on cone-beam CT images", SPIE Vol. 2163, pp. 184, Phys. of Med. Imag., 1994), the number of projection images is small, and the like.

It is known that even if inhomogeneity of the reconstructed images which is caused by the measuring system as mentioned above is solved, a reconstruction error is caused in the cone-beam reconstruction algorithm of Feldkamp (refer to Tsuneo Saito, "Three-dimensional Imaging—Cone-Beam 3D CT—", MED. IMAG. TECH., pp. 183, Vol. 13, No. 3, May, 1995).

From the above reasons, according to the conventional cone-beam tomographying apparatus and method, it is difficult to illustrates a branch of a detailed blood vessel. As one of the methods of solving such a problem, there is a technique proposed in JP-A-8-168487 by the applicant of the present invention. According to such a technique, as a projection image, a transmitted X-ray image (mask image) before the contrast medium is injected is used in place of the air scan image, and a cone-beam reconstruction calculation is executed by using the difference between the logarithm of the mask image and the logarithm of the transmitted X-ray image (live image) after the contrast medium was injected. By constructing as mentioned above, bones and internal organs other than contrast filled vessels and the other error factors which are commonly included in the two transmitted X-ray images (live image and mask image) can be removed, so that a high precision image of contrast filled vessels can be obtained. According to such a method, since it is an object to selectively obtain only the image of the contrast filled vessels as a reconstructed image, no consideration is paid to illustrating the positional relations between the blood vessels and the other bones and internal organs.

The objects and subjects to be solved by the present invention are the following three points:

1) To obtain an image of blood vessels preferably illustrated with a fine branch;

2) The positional relations between the blood vessels and the other bones and internal organs can be easily grasped; and 3) It is not necessary to use complicated apparatuses and to increase a calculation amount when realizing the above items 1) and 2).

According to the present invention, there is provided a method of X-ray computerized tomography whereby a scanner (scan driving part) in which an X-ray source for irradiating an X-ray in a cone-beam shape to an object and a two-dimensional detector for detecting the X-ray transmitted through the object are installed is rotated around the object and a projection angle is changed and a distribution of X-ray attenuation coefficients of the object is reconstructed from the transmitted X-ray images obtained at a plurality of projection angles, wherein the method of X-ray computerized tomography is characterized by comprising the steps of:

(1) measuring a first transmitted X-ray image measured in a state in which a contrast medium is injected into the object, a second transmitted X-ray image measured in a state in which no contrast medium is injected into the object, and a third transmitted X-ray image measured in a state in which no object is positioned in the apparatus;

(2) calculating a first projection image from a difference between logarithms of the first and second transmitted X-ray images obtained at the same projection angle, calculating a second projection image from a difference between logarithms of the second and third transmitted X-ray images obtained at the same projection angle, and simultaneously reconstructing a first reconstructed image from the first projection image and a second reconstructed image from the second projection image in parallel; and (3) composing the first and second reconstructed images, thereby forming a composed image.

According to the invention, there is also provided an X-ray computerized tomography apparatus comprising a scanner (scan driving part) in which an X-ray source for irradiating an X-ray in a cone-beam shape to an object and a two-dimensional detector for detecting the X-ray transmitted through the object are installed and means for rotating the scanner around the object, changing a projection angle, and reconstructing a distribution of X-ray attenuation coefficients of the object from the transmitted X-ray images obtained at a plurality of projection angles, wherein the X-ray tomographing apparatus is characterized by comprising:

memory means (memory medium) for storing a first transmitted X-ray image measured in a state in which a contrast medium is injected into the object, a second transmitted X-ray image measured in a state in which no contrast medium is injected into the object, and a third transmitted X-ray image measured in a state in which the object is not put in the apparatus;

calculating means (computer) for respectively calculating a first projection image from a difference between logarithms of the first and second transmitted X-ray images obtained at the same projection angle, calculating a second projection image from a difference between logarithms of the second and third transmitted X-ray images obtained at the same projection angle, and simultaneously reconstructing a first reconstructed image from the first projection image and a second reconstructed image from the second projection image in parallel; and imaging processing means for forming a composed image from the first and second reconstructed images.

When summarizing the invention, the projection image (blood vessel projection image) obtained by the difference between the logarithm of the mask image and the logarithm of the live image obtained at the same projection angle is reconstructed, thereby obtaining a reconstructed blood vessel image. At the same time, by reconstructing the projection image (background projection image) obtained by the difference between the logarithm of the mask image and the logarithm of the air scan image, a reconstructed background image is obtained. A composed image of the reconstructed blood vessel image and the reconstructed background image is formed. Thus, the blood vessel image in which the fine branch is also preferably illustrated and the reconstructed image in which the positional relations between the blood vessels and the other bones and internal organs can be easily grasped can be obtained.

DESCRIPTION OF THE PREFERRED EMBODIMENTS

In X-ray tomographying method and apparatus according to the invention, a reconstructed image is formed as follows. First, a projection image obtained by a difference between logarithms of a mask image and a live image obtained at a same projection angle (hereinafter, such an image is referred to as a "blood vessel projection image") is reconstructed, thereby obtaining a reconstructed blood vessel image. At the same time, a projection image obtained by a difference between logarithms of the mask image and the air scan image (hereinafter, such an image is referred to as a "background projection image") is reconstructed, thereby obtaining a reconstructed background image. The "reconstructed background image" disclosed here denotes a reconstructed image constructed by all of the other bones, internal organs, muscles, fat, contrast non-filled vessels, and the like which don't include the contrast filled vessels in an object. A composed image of the reconstructed blood vessel image and the reconstructed background image is formed. In this instance, reconstruction calculations of the reconstructed blood vessel image and the reconstructed background image are simultaneously executed in parallel as follows. First, in a filtering process, a blood vessel projection image is stored into a real part and a background projection image at the same projection angle is stored in an imaginary part and two sets of projection images are filtered at once. Then, in a backprojection process, a calculation of coordinates is performed only once and a calculation result is used for the backprojection process of two sets of projection images at the corresponding same projection angle. When the reconstructed blood vessel image and the reconstructed background image are composed, a parameter for visualizing is individually set in each of the reconstructed blood vessel image and the reconstructed background image so that a region of interest can be preferably illustrated. An embodiment of the invention will now be described in detail hereinbelow with reference to the drawings.

Figure 1:
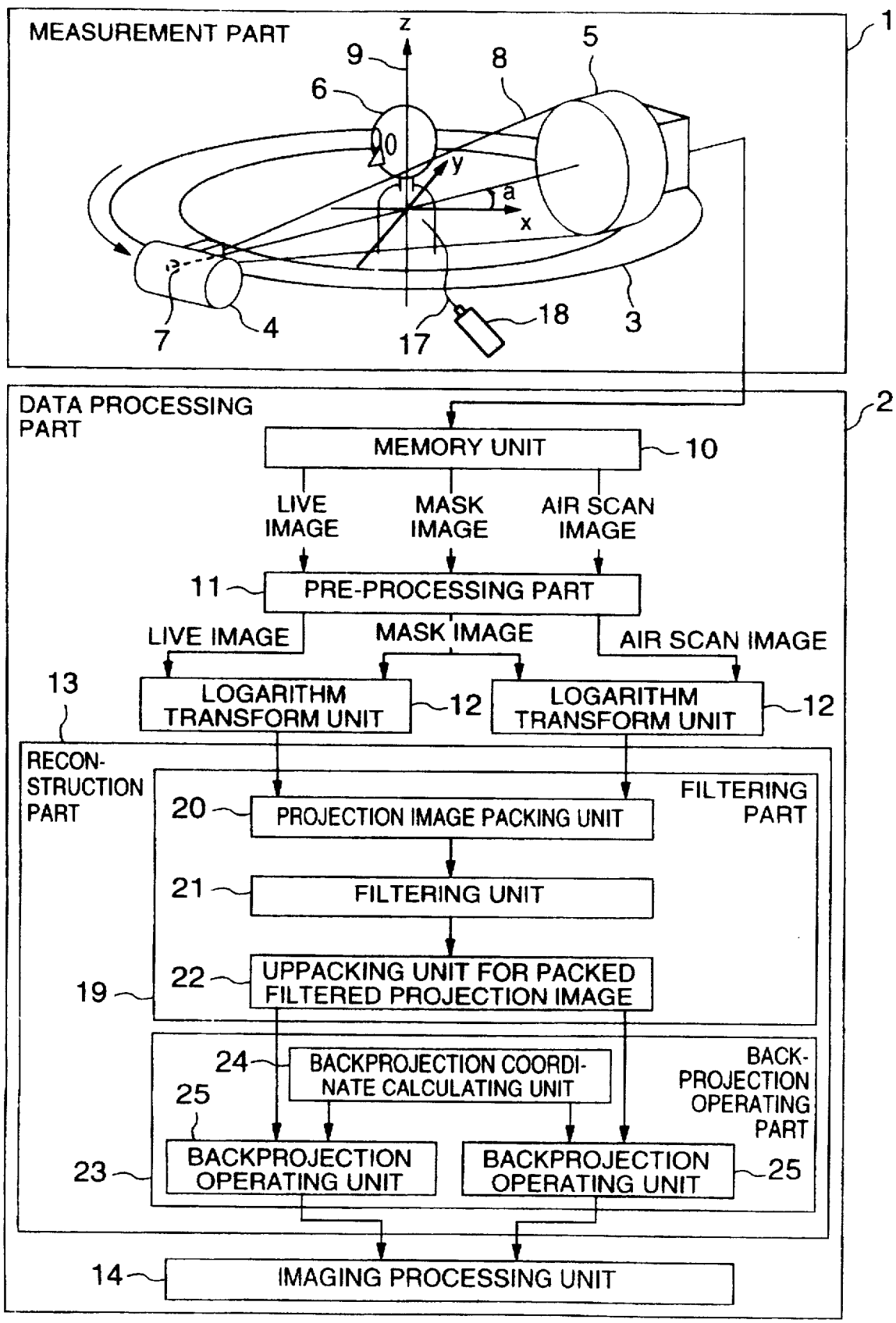
FIG. 1 is a block constructional diagram of a cone-beam X-ray tomographying apparatus according to an embodiment of the invention.
Figure 2:
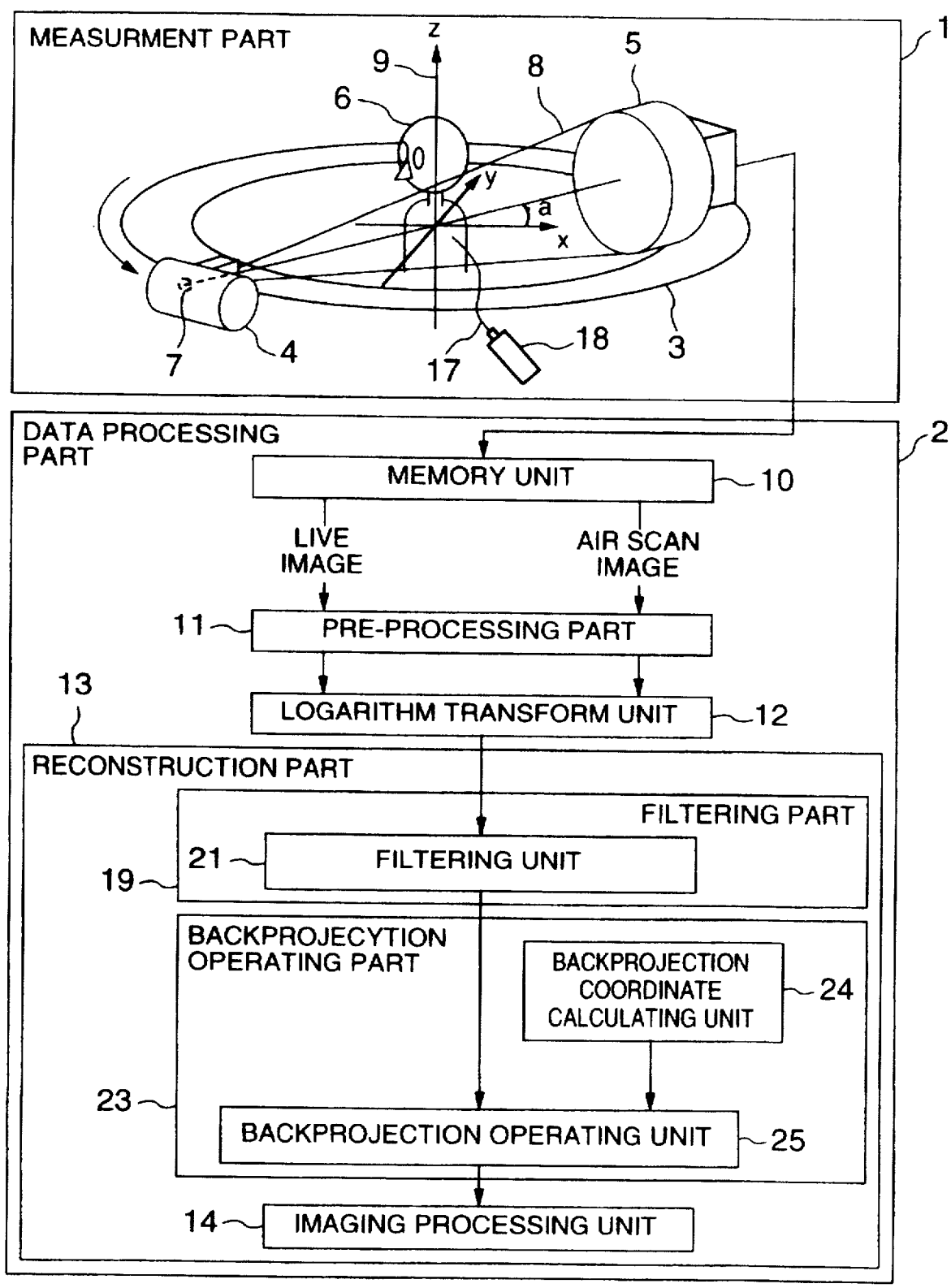
FIG. 2 is a diagram showing an example of a conventional cone-beam X-ray tomographying apparatus.
Figure 3:
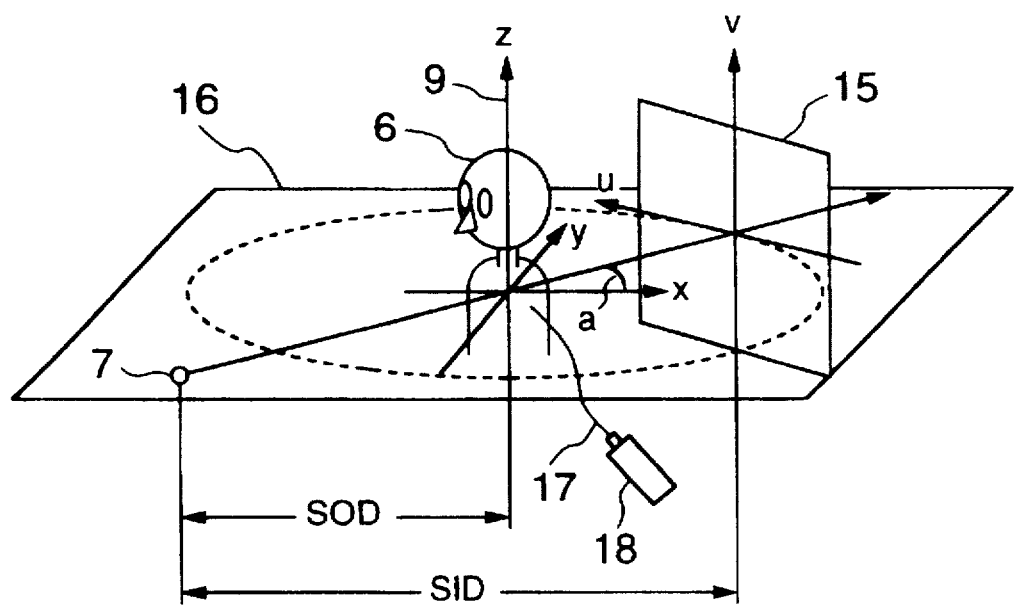
FIG. 3 is a diagram showing a geometrical relation of a measurement part in the conventional general cone-beam X-ray tomographying apparatus.
Figure 4:
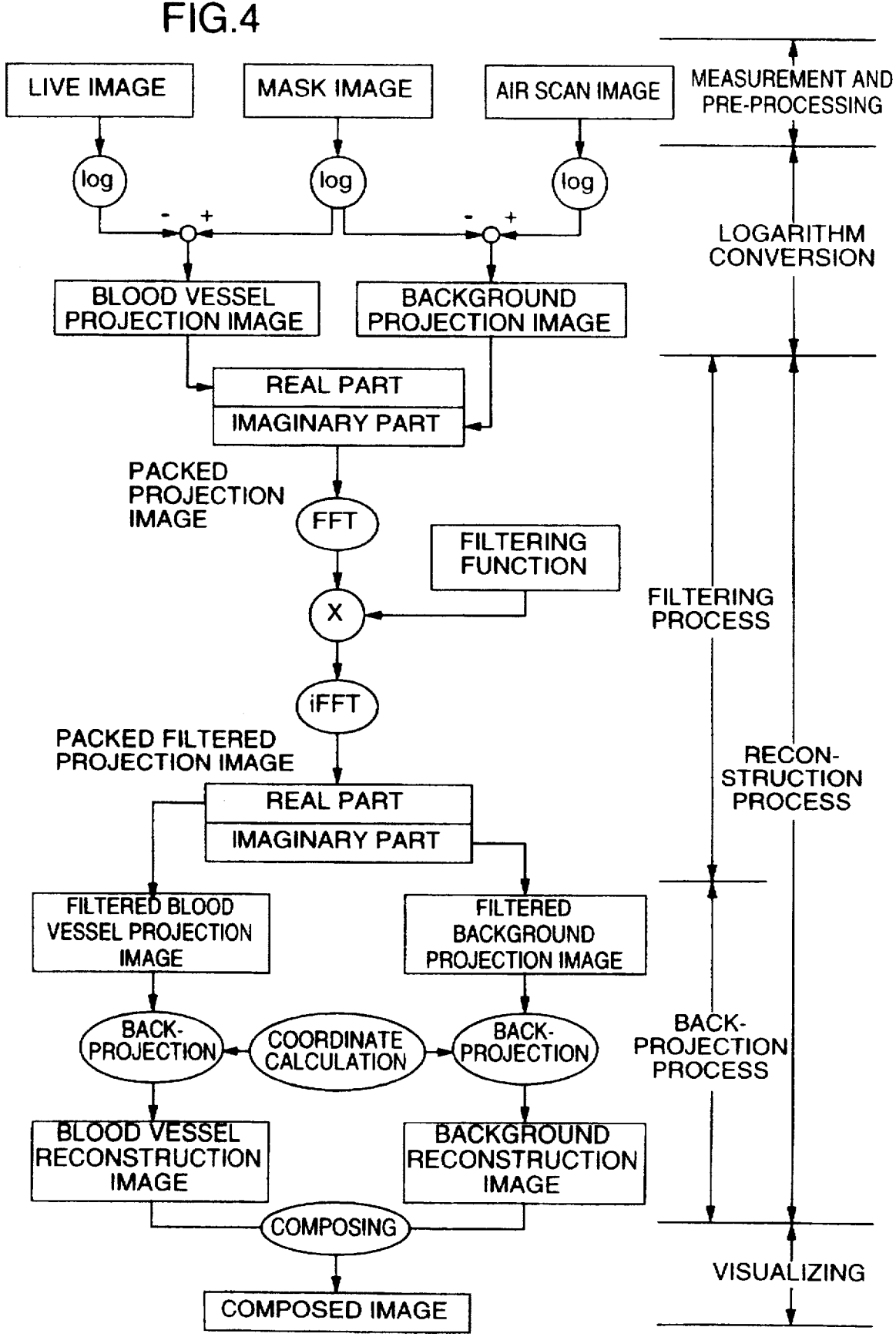
FIG. 4 is a diagram showing a flow of processes in the embodiment of the invention.
Figure 5:
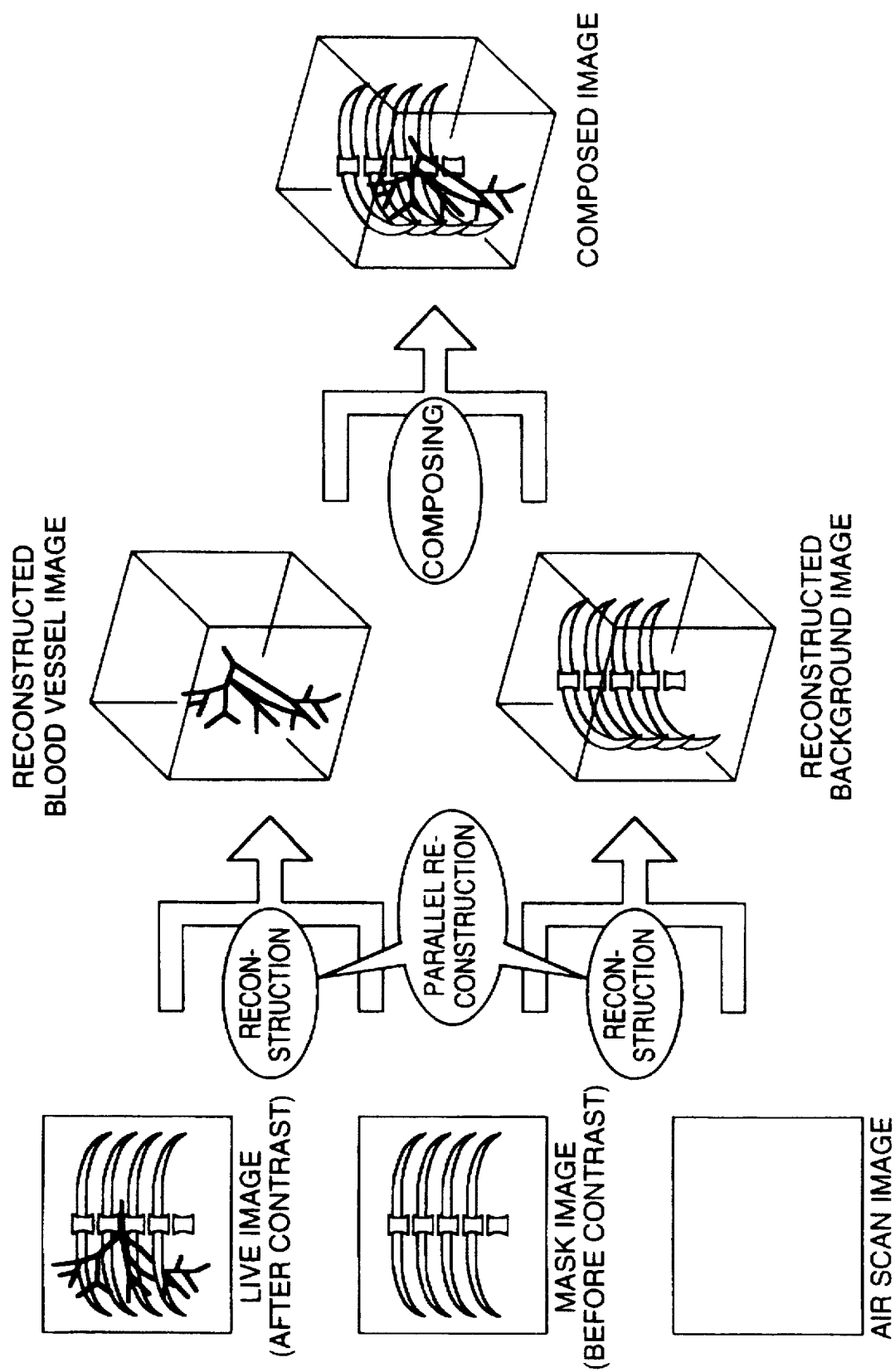
FIG. 5 is a diagram showing an example of a specific image in the embodiment of the invention.

FIG. 1 is a block diagram showing a cone-beam X-ray tomographying apparatus according to an embodiment of the invention. FIG. 4 shows a data processing procedure in the embodiment. FIG. 5 shows an example of a specific image. The details of a cone-beam reconstruction operating method according to the invention will now be sequentially explained hereinbelow. First, no contrast medium is injected into the object 6, the X-ray 8 in a cone-beam shape is irradiated from the X-ray source 4, the scanner 3 is rotated once, and transmitted X-ray images of the number corresponding to the whole circumference are obtained by the two-dimensional detector 5 and held in the memory unit (memory medium) 10. If necessary, a geometric distortion correction or the like is performed to the transmitted X-ray images and the resultant images are used as mask images Imask(a,u,v).

A contrast medium is subsequently injected into the object 6, the cone-beam shaped X-ray 8 is irradiated from the X-ray source 4 in a manner similar to the above, the scanner 3 is rotated once, and the transmitted X-ray images of the number as many as the whole circumference are obtained by the two-dimensional X-ray detector 5 and held in the memory unit 10. Similarly, a geometric distortion correction or the like is performed to the transmitted X-ray images as necessary and the resultant images are set to live images Ilive(a,u,v). The contrast medium is injected by a method of selectively injecting into a desired blood vessel by using the catheter 17 and contrast injector 18 or by a method by a drip (intravenous contrast administration). Although the mask images and live images are obtained by the foregoing method, such a procedure is almost the same as the procedure for obtaining transmitted X-ray images before and after the contrast injection in the conventional technique known as a DSA (Digital Subtraction Angiography). The embodiment differs from the DSA with respect to a point that it is necessary to obtain the transmitted X-ray images of the number corresponding to the whole circumference by rotating a pair of X-ray source 4 and tow-dimensional detector 5 on the scanner 3.

Separately from the foregoing measurement, no object is positioned, the cone-beam shaped X-ray 8 is irradiated from the X-ray source 4, the scanner 3 is rotated once, and the transmitted X-ray images of the number corresponding to the whole circumference are obtained by the two-dimensional detector 5 and held in the memory unit 10. Similarly, the geometric distortion correction or the like is performed to the transmitted X-ray images as necessary and the resultant images are set to air scan images Iair(a,u,v). The air scan images are obtained before or after the object 6 is/was photographed. It is also possible to once obtain the air scan images and to repetitively use them. Ideally, it is desirable that X-ray conditions when obtaining the air scan images are the same as those when the mask images and live images are obtained.

Two kinds of projection images which are necessary for the reconstruction calculation are formed from the mask images, live images, and air scan images at the same projection angle obtained as mentioned above. First, in the log transform unit 12, a blood vessel projection image Pv(a,u,v) is formed from the difference between logarithms of the mask image and the live image. Namely, $$Pv(a,u,v)=\log\{Imask(a,u,v)\}-\log\{Ilive(a,u,v)\}$$

is obtained. Similarly, in the logarithm transform unit 12, a background projection image Pb(a,u,v) is formed from the difference between logarithms of the mask image and the air scan image. Namely, $$Pb(a,u,v)=\log\{Iair(a,u,v)\}-\log\{Imask(a,u,v)\}$$

is obtained.

In the reconstruction part 13, a reconstructed blood vessel image and a reconstructed background image are subsequently reconstructed from the blood vessel projection image and the background projection image. The above reconstruction calculations are simultaneously executed in parallel. First, in a filtering part 19, a filtering of the projection images is performed. The filtering process is constructed by three stages of 1) a packing of the projection images, 2) a filtering, and 3) an unpacking of the packed filtered projection image in the embodiment. In correspondence to them, the filtering part 19 is constructed by projection image packing unit 20, filtering unit 21, and unpacking unit 22 for the packed filtered projection image.

First, in the packing process of the projection images, a packed projection image Pvb(a,u,v) in which the blood vessel projection image is a real part and the background projection image is an imaginary part is obtained. Namely, $$Pvb(a,u,v) = Pv(a,u,v) + kPb(a,u,v)$$

where, k is an imaginary unit and k2=(−1). A filtering as shown by the following equation (3) is subsequently performed to the packed projection image Pvb(a,u,v), thereby obtaining a filtered projection image Qvb(a,u,v) (referred to as a "packed filtered projection image").

$$Qvb(a, u, v) = \qquad (3)$$

$$iFFT \left\{ FFT \left\{ \frac{SOD}{SOD^2 + u^2 + v^2} Pvb(a, u, v) \right\} \cdot FFT\{h(u)\} \right\}$$

In the unpacking process of the packed filtered projection image, the real part of the packed filtered projection image Qvb(a,u,v) obtained is separated as a filtered blood vessel projection image Qv(a,u,v) and the imaginary part is separated as a filtered background projection image Qb(a,u,v). It is also obviously possible to execute a filtering to the packed projection image in which the blood vessel projection image is set to the imaginary part and the background projection image is set to the real part, to separate the imaginary part of the packed filtered projection image as a filtered blood vessel projection image, and to separate the real part as a filtered background projection image. In the conventional filtering, the imaginary part of the projection image is filled with zero (0) before the filtering process and only the real part is used even after the filtering process. Therefore, if it is intended to performing the filtering process to the blood vessel projection image and the background projection image, it is necessary to separately execute the calculations.

On the other hand, according to the embodiment, as mentioned above, by executing the filtering process to the packed projection image, the filtering for the two projection images of the blood vessel projection image and the background projection image can be simultaneously and independently executed owing to the characteristics of the Fourier transformation, so that the calculating time can be remarkably reduced. Even in a backprojection calculation, in the embodiment, the calculating time can be also reduced by the following method. In the embodiment, a backprojection operating part 23 is constructed by a backprojection coordinate calculating unit 24 and a backprojection operating unit 25 for reconstructing a blood vessel image and a background image.

As described above with respect to the prior art, first at the projection angle (a), backprojection coordinates (u',v') to be backprojected for the point (x,y,z) is calculated in accordance with the following equations (4). The backprojection coordinates are determined by only a geometrical construction of the measurement part 1 irrespective of the object 6 and photographing conditions. Therefore, the calculation result of the backprojection coordinates can be shared in the backprojection calculations of the reconstructed blood vessel image and the reconstructed background image. In the embodiment, in the backprojection calculations of the reconstructed blood vessel image and the reconstructed background image, the same backprojection coordinates as those calculated by the backprojection operating unit 25 are used.

$$\left. \begin{array}{l} u' = \dfrac{SID}{SOD + x\cos(a) + y\sin(a)} \cdot (-x\sin(a) + y\cos(a)) \\ v' = \dfrac{SID}{SOD + x\cos(a) + y\sin(a)} \cdot z \end{array} \right\} \qquad (4)$$

Now, assuming that the reconstructed blood vessel image is set to fv(x,y,z) and the reconstructed background image is set to fb(x,y,z), the backprojection calculations can be executed in accordance with the following equations (5).

$$\left. \begin{array}{l} fv(x, y, z) = \displaystyle\int_0^{2\pi} \dfrac{SOD^2}{(SOD + x\cos(a) + y\sin(a))^2} Qv(a, u', v') da \\ fb(x, y, z) = \displaystyle\int_0^{2\pi} \dfrac{SOD^2}{(SOD + x\cos(a) + y\sin(a))^2} Qb(a, u', v') da \end{array} \right\} \qquad (5)$$

Since a coefficient $SOD^2/\{SOD+x\cos(a)+y\sin(a)\}^2$ appearing in the equation (5) is also common in the backprojection calculations of both of the reconstructed blood vessel image and the reconstructed background image, it is also possible to calculate the coefficient by the backprojection coordinate operating unit 24 and to share it. As another embodiment, it is also possible to use a method whereby the backprojection coordinates (u',v') are once calculated for all of a, x, y, and z and are held in memory means having a large memory capacity such as a hard disk or the like and are used for the reconstruction calculation every time. As mentioned above, two reconstructed images, namely, the reconstructed blood vessel image and the reconstructed background image are separately obtained and are individually visualized or are composed and visualized by the imaging processing unit 14. FIG. 5 shows a specific example of such a visualization.

Since the reconstructed blood vessel image which is displayed is an image in which only the contrast filled vessels of the object 6 are selectively reconstructed, the bones and internal organs other than the contrast filled blood vessels and the other error factors can be removed, so that an image in which a branch of fine blood vessels and the like are preferably illustrated. As already described with respect to the prior art, however, it is difficult to grasp the relative positional relations between the blood vessels and the bones, internal organs, and the like by only the reconstructed blood vessel image. In the embodiment, therefore, as shown in FIG. 5, a composed image obtained by composing the reconstructed blood vessel image and the reconstructed background image is formed. The composed image preferably illustrates the fine branch of the blood vessels or the like and clearly shows the relative positional relations between the blood vessels and the bones, internal organs, and the like.

As a visualizing method of the reconstructed image, for example, there is a volume rendering method, a maximum intensity projection method, or the like. According to the volume rendering method, for example, when it is intended to illustrate a branch of the fine blood vessels, background noises are emphasized and, on the contrary, when it is intended to make the noises inconspicuous, the branch of the fine blood vessels is not illustrated. A delicate adjustment is, therefore, required to set parameters. In the embodiment, when the reconstructed blood vessel image and the reconstructed background image are obtained, parameters for visualizing are independently set. Therefore, in each reconstructed image, the parameters can be adjusted so that a target portion is properly illustrated. After the volume rendering was performed in each parameter, by composing the images in which depth information has been preserved, an image in which the relative positional relations between the blood vessels and the other bones and internal organs are reflected can be obtained.

When visualizing by the maximum intensity projection method, by applying a proper weight to each of the reconstructed blood vessel image and the reconstructed background image and by adding the weighted images, a desired image can be easily derived. According to the above embodiment, a three-dimensional image which preferably illustrates the fine branch of the blood vessels or the like and preferably shows the relative positional relations between the blood vessels and the bones, internal organs, and the like can be obtained. The above embodiment shows an example of the invention and the invention is not limited to it.

As described in detail above, according to the invention, a blood vessel image in which the fine branch is also preferably illustrated can be obtained without causing a complication of the apparatus and without needing an increase in calculation amount. The positional relations between the blood vessels and the other bones and internal organs can be easily grasped.

More specific effects of the invention are as follows. Since the selective reconstruction of only the reconstructed blood vessel image is executed, the reconstructed blood vessel image in which up to the fine portion is illustrated can be obtained. Since the reconstructed blood vessel image is composed with the reconstructed background image, the relative positional relations between the blood vessels and the other bones and internal organs can be easily grasped. Further, when the reconstructed blood vessel image and the reconstructed background image are composed, since the parameters for visualization are individually set in each of the reconstructed blood vessel image and the reconstructed background image, it is possible to adjust so that the target portion is properly illustrated in each image. Further, since the reconstructions of the reconstructed blood vessel image and the reconstructed background image are simultaneously executed in parallel in the reconstruction calculation, as compared with the method of individually performing the reconstructions of two times, the calculating time can be reduced into about ⅔.

What is claimed is:

1. A method of X-ray computerized tomography whereby a scanner in which an X-ray source for irradiating an X-ray in a cone-beam shape to an object and a two-dimensional detector for detecting the X-ray transmitted through said object are installed is rotated around said object and a projection angle is changed and a distribution of X-ray attenuation coefficients of said object is reconstructed from transmitted X-ray images obtained at a plurality of said projection angles, comprising the steps of:

(1) measuring a first transmitted X-ray image measured in a state in which a contrast medium is injected into said object, a second transmitted X-ray image measured in a state in which no contrast medium is injected into said object, and a third transmitted X-ray image measured in a state in which no object is positioned in the apparatus, all at the same projection angle;
  (2) calculating a first projection image from a difference between logarithms of said first and second transmitted X-ray images obtained at said same projection angle, calculating a second projection image from a difference between logarithms of said second and third transmitted X-ray images obtained at said same projection angle, and simultaneously reconstructing a first reconstructed image from said first projection image and a second reconstructed image from said second projection image in parallel; and
  (3) composing said first and second reconstructed images, thereby forming a composed image.

2. A method according to claim 1, wherein on said transmitted X-ray images, when a u axis is set to a rotation tangential direction of said scanner and a v axis is set to a rotation center axial direction of said scanner, at a projection angle (a), now assuming that said first transmitted X-ray image is set to I1(a,u,v), said second transmitted X-ray image is set to I2(a,u,v), said third transmitted X-ray image is set to I3(a,u,v), said first projection image is set to P1(a,u,v), and said second projection image is set to P2(a, u,v), in said step (2), said first projection image P1(a,u,v) and said second projection image P2(a,u,v) are calculated in accordance with the following equations (a):

$$\left. \begin{array}{l} P1(a, u, v) = \log(I2(a, u, v)) - \log(I1(a, u, v)) \\ P2(a, u, v) = \log(I3(a, u, v)) - \log(I2(a, u, v)) \end{array} \right\} \quad (a).$$

3. A method according to claim 1, wherein in said step (2), a reconstruction calculation for simultaneously reconstructing in parallel said first and second reconstructed images includes a filtering process, and in said filtering process, said first and second projection images obtained at said same projection angle are packed to thereby form a packed projection image, said packed projection image is filtered to thereby obtain a packed filtered projection image, and a first filtered projection image and a second filtered projection image are unpacked from said packed filtered projection image.

4. A method according to claim 3, wherein the reconstruction calculation for simultaneously reconstructing in parallel said first and second reconstructed images further includes a backprojection process, and in said backprojection process, backprojection coordinates on the projection image to be backprojected to coordinates on the reconstructed image are calculated, and when said first reconstructed image is backprojected from said first filtered projection image obtained at said same projection angle and said second reconstructed image is backprojected from said second filtered projection image obtained at said same projection angle, a backprojection calculation is executed by using said same backprojection coordinates.

5. A method according to claim 4, wherein the calculation of said backprojection coordinates is a calculation such that when a rotation center axis of said scanner is set to a z axis and fixed xyz coordinates are determined on said object and the reconstructed image is set to f(x,y,z), a point (u',v') on the projection image at a projection angle (a) to be backprojected to a point (x,y,z) on said xyz coordinates is obtained, and assuming that SID denotes a distance between said X-ray source and said detector and SOD denotes a distance between said X-ray source and the rotation center, said backprojection coordinates (u',v') are calculated in accordance with the following equations (b):

$$\left. \begin{array}{l} u' = \dfrac{SID}{SOD + x\cos(a) + y\sin(a)} \cdot (-x\sin(a) + y\cos(a)) \\ v' = \dfrac{SID}{SOD + x\cos(a) + y\sin(a)} \cdot z \end{array} \right\} \quad (b).$$

6. A method according to claim 3, wherein in the formation of said packed projection image, data constructed by a complex number in which said first projection image obtained at said same projection angle is set to a real part and said second projection image obtained at said same projection angle is set to an imaginary part is set to said packed projection image or data constructed by a complex number in which said first projection image is set to an imaginary part and said second projection image is set to a real part is set to said packed projection image.

7. A method according to claim 3, wherein
in the unpacking of said first and second filtered projection images from said packed filtered projection image,
a real part of said packed filtered projection image obtained at said same projection angle is set to said first filtered projection image and an imaginary part is set to said second filtered projection image, or the imaginary part of said packed filtered projection image is set to said first filtered projection image and the real part is set to said second filtered projection image.

8. A method of X-ray computerized tomography whereby a scanner in which an X-ray source for irradiating an X-ray in a cone-beam shape to an object and a two-dimensional detector for detecting the X-ray transmitted through said object are installed is rotated around said object and a projection angle is changed and a distribution of X-ray attenuation coefficients of said object is reconstructed from transmitted X-ray images obtained at a plurality of said projection angles, comprising the steps of:

(1) measuring a first transmitted X-ray image measured in a state in which a contrast medium is injected into said object, a second transmitted X-ray image measured in a state in which no contrast medium is injected into said object, and a third transmitted X-ray image measured in a state in which no object is positioned in the apparatus, all at the same projection angle;

(2) calculating a first projection image from a difference between logarithms of said first and second transmitted X-ray images obtained at said same projection angle, calculating a second projection image from a difference between logarithms of said second and third transmitted X-ray images obtained at said same projection angle, and simultaneously reconstructing a first reconstructed image from said first projection image and a second reconstructed image from said second projection image in parallel; and (3) composing said first and second reconstructed images, thereby forming a composed image, wherein in said step (2), a reconstruction calculation for simultaneously reconstructing in parallel said first and second reconstructed images includes a filtering process, and in said filtering process, said first and second projection images obtained at said same projection angle are packed to thereby form a packed projection image, said packed projection image is filtered to thereby obtain a packed filtered projection image, and a first filtered projection image and a second filtered projection image are unpacked from said packed filtered projection image, in the formation of said packed projection image, data constructed by a complex number in which said first projection image obtained at said same projection angle is set to a real part and said second projection image obtained at said same projection angle is set to an imaginary part is set to said packed projection image or data constructed by a complex number in which said first projection image is set to an imaginary part and said second projection image is set to a real part is set to said packed projection image, and in the unpacking of said first and second filtered projection images from said packed filtered projection image, a real part of said packed filtered projection image obtained at said same projection angle is set to said first filtered projection image and an imaginary part is set to said second filtered projection image, or the imaginary part of said packed filtered projection image is set to said first filtered projection image and the real part is set to said second filtered projection image.

9. An apparatus of X-ray computerized tomography comprising a scanner in which an X-ray source for irradiating an X-ray in a cone-beam shape to an object and a two-dimensional detector for detecting the X-ray transmitted through said object are installed and means for rotating said scanner around said object, changing a projection angle, and reconstructing a distribution of X-ray attenuation coefficients of said object from the transmitted X-ray images obtained at a plurality of said projection angles, comprising:

memory means for storing a first transmitted X-ray image measured in a state in which a contrast medium is injected into said object, a second transmitted X-ray image measured in a state in which no contrast medium is injected into said object, and a third transmitted X-ray image measured in a state in which no object is positioned in the apparatus, all at the same projection angle;

calculating means for respectively calculating a first projection image from a difference between logarithms of said first and second transmitted X-ray images obtained at said same projection angle, calculating a second projection image from a difference between logarithms of said second and third transmitted X-ray images obtained at said same projection angle, and simultaneously reconstructing a first reconstructed image from said first projection image and a second reconstructed image from said second projection image in parallel; and imaging processing means for forming a composed image from said first and second reconstructed images.

10. An apparatus according to claim 9, wherein on said transmitted X-ray images, when a u axis is set to a rotation tangential direction of said scanner and a v axis is set to a rotation center axial direction of said scanner, at a projection angle (a), now assuming that said first transmitted X-ray image is set to I1(a,u,v), said second transmitted X-ray image is set to I2(a,u,v), said third transmitted X-ray image is set to I3(a,u,v), said first projection image is set to P1(a,u,v), and said second projection image is set to P2(a, u,v), said calculating means calculates said first projection image P1(a,u,v) and said second projection image P2(a,u,v) in accordance with the following equations (c):

$$\left. \begin{array}{l} P1(a, u, v) = \log(I2(a, u, v)) - \log(I1(a, u, v)) \\ P2(a, u, v) = \log(I3(a, u, v)) - \log(I2(a, u, v)) \end{array} \right\} \quad (c).$$

11. An apparatus according to claim 9, wherein said calculating means includes a filtering operating part, said filtering operating part has: projection image packing means for forming a packed projection image by packing said first and second projection images obtained at said same projection angle; filtering means for obtaining packed filtered projection image by filtering said packed projection image; and filtered projection image unpacking means for unpacking said first and second filtered projection images from said packed filtered projection image.

12. An apparatus according to claim 11, wherein said calculating means further includes a backprojection operating part, and said backprojection operating part has: backprojection coordinate calculating means for calculating backprojection coordinates on a projection image to be backprojected to coordinates on the reconstructed image; and backprojection operating means for performing a backprojection calculation by using said same backprojection coordinates when said first reconstructed image is backprojected from said first filtered projection image obtained at said same projection angle and said second reconstructed image is backprojected from said second filtered projection image obtained at said same projection angle.

13. An apparatus according to claim 12, wherein said backprojection coordinate calculating means executes a calculation such that when a rotation center axis of said scanner is set to a z axis and fixed xyz coordinates are determined on said object and the reconstructed image is set to f(x,y,z), a point (u',v') on the projection image at a projection angle (a) to be backprojected to a point (x,y,z) on said xyz coordinates is obtained, and assuming that SID is set to a distance between said X-ray source and said detector and SOD denotes a distance between said X-ray source and the rotation center, said backprojection coordinates (u',v') are calculated in accordance with the following equations (d):

$$u' = \frac{SID}{SOD + x\cos(a) + y\sin(a)} \cdot (-x\sin(a) + y\cos(a))$$
$$v' = \frac{SID}{SOD + x\cos(a) + y\sin(a)} \cdot z \qquad (d).$$

14. An apparatus according to claim 11, wherein in said projection image packing means, data constructed by a complex number in which said first projection image obtained at said same projection angle is set to a real part and said second projection image obtained at said same projection angle is set to an imaginary part is set to said packed projection image or data constructed by a complex number in which said first projection image is set to an imaginary part and said second projection image is set to a real part is set to said packed projection image.

15. An apparatus according to claim 11, wherein in said filtered projection image unpacking means, a real part of said packed filtered projection image obtained at said same projection angle is set to said first filtered projection image and an imaginary part is set to said second filtered projection image, or the imaginary part of said packed filtered projection image is set to said first filtered projection image and the real part is set to said second filtered projection image.

16. A apparatus of X-ray computerized tomography comprising a scanner in which an X-ray source for irradiating an X-ray in a cone-beam shape to an object and a two-dimensional detector for detecting the X-ray transmitted through said object are installed and means for rotating said scanner around said object, changing a projection angle, and reconstructing a distribution of X-ray attenuation-coefficients of said object from the transmitted X-ray images obtained at a plurality of said projection angles, comprising:

memory means for storing a first transmitted X-ray image measured in a state in which a contrast medium is injected into said object, a second transmitted X-ray image measured in a state in which no contrast medium is injected into said object, and a third transmitted X-ray image measured in a state in which no object is positioned in the apparatus, all at the same projection angle;

calculating means for respectively calculating a first projection image from a difference between logarithms of said first and second transmitted X-ray images obtained at said same projection angle, calculating a second projection image from a difference between logarithms of said second and third transmitted X-ray images obtained at said same projection angle, and simultaneously reconstructing a first reconstructed image from said first projection image and a second reconstructed image from said second projection image in parallel; and imaging processing means for forming a composed image from said first and second reconstructed images, wherein said calculating means includes a filtering operating part, said filtering operating part has: projection image packing means for forming a packed projection image by packing said first and second projection images obtained at said same projection angle; filtering means for obtaining packed filtered projection image by filtering said packed projection image; and filtered projection image unpacking means for unpacking said first and second filtered projection images from said packed filtered projection image, in said projection image packing means, data constructed by a complex number in which said first projection image obtained at said same projection angle is set to a real part and said second projection image obtained at said same projection angle is set to an imaginary part is set to said packed projection image or data constructed by a complex number in which said first projection image is set to an imaginary part and said second projection image is set to a real part is set to said packed projection image, and in said filtered projection image unpacking means, a real part of said packed filtered projection image obtained at said same projection angle is set to said first filtered projection image and an imaginary part is set to said second filtered projection image, or the imaginary part of said packed filtered projection image is set to said first filtered projection image and the real part is set to said second filtered projection image.

17. An apparatus of X-ray computerized tomography comprising a scanner in which an X-ray source for irradiating an X-ray in a cone-beam shape to an object and a two-dimensional detector for detecting the X-ray transmitted through said object are installed and means for rotating said scanner around said object, changing a projection angle, and reconstructing a distribution of X-ray attenuation coefficients of said object from the transmitted X-ray images obtained at a plurality of said projection angles, comprising:

a memory medium for storing a first transmitted X-ray image measured in a state in which a contrast medium is injected into said object, a second transmitted X-ray image measured in a state in which no contrast medium is injected into said object, and a third transmitted X-ray image measured in a state in which no object is positioned in the apparatus, all at the same projection angle; and a computer for respectively calculating a first projection image from a difference between logarithms of said first and second transmitted X-ray images obtained at said same projection angle, calculating a second projection image from a difference between logarithms of said second and third transmitted X-ray images obtained at said same projection angle, simultaneously reconstructing a first reconstructed image from said first projection image and a second reconstructed image from said second projection image in parallel, and forming a composed image from said first and second reconstructed images.

* * * * *